United States Patent [19]

Lukacs et al.

[11] 4,043,928

[45] Aug. 23, 1977

[54] SERUM SEPARATING COMPOSITION OF MATTER

[75] Inventors: Michel J. Lukacs, Goshen, N.Y.; Ian H. Jacoby, Franklin Lakes, N.J.

[73] Assignee: Lukacs and Jacoby Associates, Middletown, N.Y.

[21] Appl. No.: 411,239

[22] Filed: Oct. 31, 1973

[51] Int. Cl.² .......................... B29F 3/00; C09K 3/00
[52] U.S. Cl. ...................................... 252/60; 252/309
[58] Field of Search .................. 252/60, 309, 317, 28; 106/287 SB; 210/83, 65

[56] References Cited

U.S. PATENT DOCUMENTS

| | | | |
|---|---|---|---|
| 2,978,298 | 4/1961 | Wetzel et al. | 252/317 |
| 3,639,260 | 2/1972 | Michalski | 252/309 |
| 3,705,860 | 12/1972 | Duvall | 252/309 |
| 3,780,935 | 12/1973 | Lukacs | 233/1 A |
| 3,780,935 | 12/1973 | Lukacs et al. | 210/65 |
| 3,882,033 | 5/1975 | Wright | 252/75 |

Primary Examiner—Benjamin R. Padgett
Assistant Examiner—Josephine Lloyd

[57] ABSTRACT

The separation of a sample of blood into serum and clot portions is accomplished by means of a sealant consisting essentially of a silicone fluid and silica dispersed therein. The separation is accomplished by inserting a supply of the sealant into a container holding a sample of the blood. The container and device are centrifuged so that it separates into serum and clot portions and the sealant, having a specific gravity of at least 1.026, separates the two portions.

4 Claims, 8 Drawing Figures

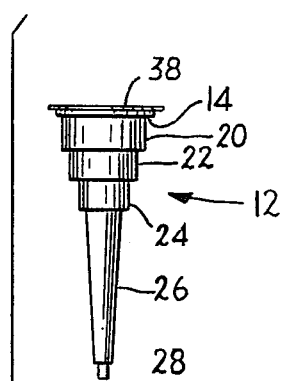
FIG. 1
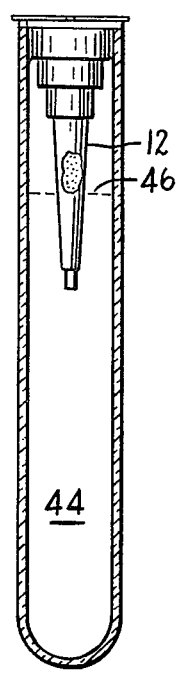
FIG. 2
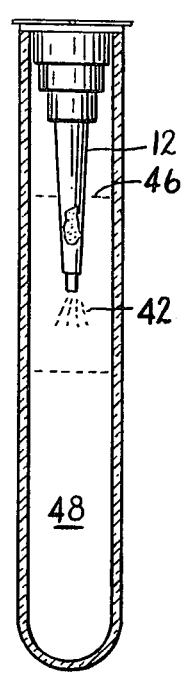
FIG. 3
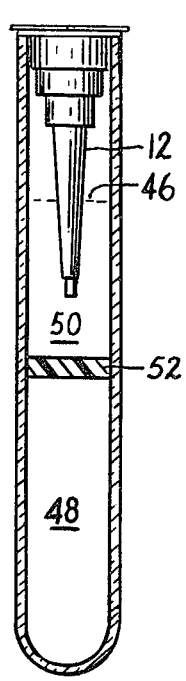
FIG. 4
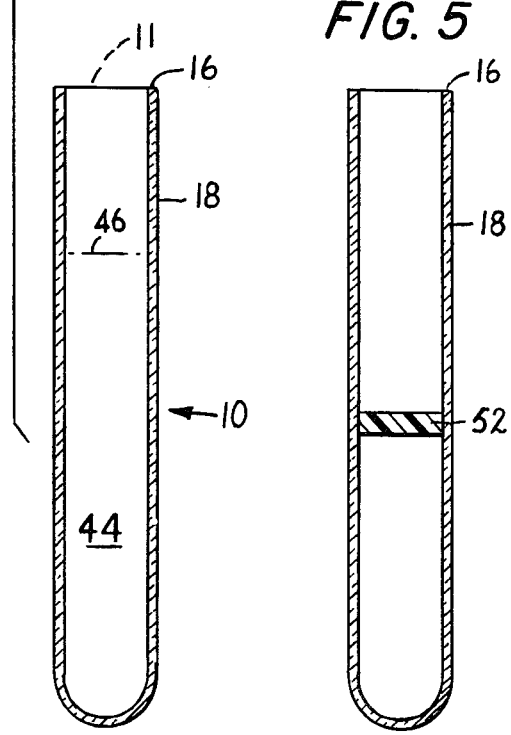
FIG. 5
FIG. 6
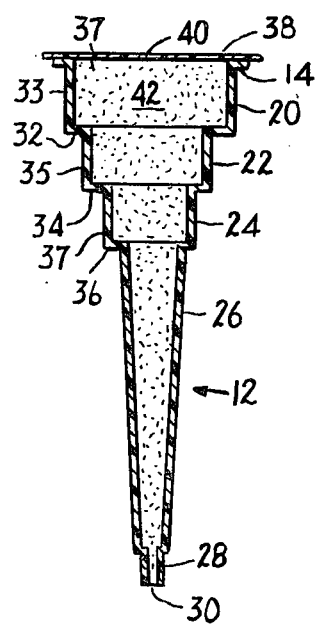
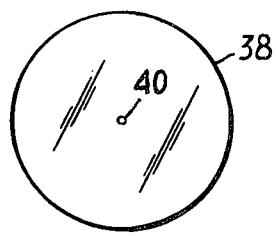
FIG. 7
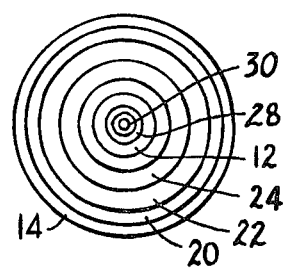
FIG. 8

SERUM SEPARATING COMPOSITION OF MATTER

BACKGROUND OF THE INVENTION

This invention relates to a composition of matter usable for separating a blood sample by a centrifuging into clot portions, so that the serum may be quickly and readily removed without contamination by the clot portion; this application is a division of copending application Ser. No. 270,278, filed July 10, 1972 and entitled "Serum Separating Method", the disclosure of said application being incorporated herein by reference.

In recent years, biomedical and hospital laboratories have been faced with increasing demands for more and more routine, as well as specialized, diagnostic tests of blood samples. To meet the demands of these tests equipment has been devised which automatically takes a sample or specimen of blood which has been placed in a cup and subjects it to a series of programmed tests which eventuate in a readout on a record member. While these analyzers have increased the efficiency of performing the necessary tests, a problem has continued in finding ways and means of separating the serum from the clot portion and removing the serum for analysis. Various types of tube and plug devices have been suggested by the prior art. For example, in U.S. Pat. No. 3,512,940, issued May 19, 1970, a device consisting of a tube with a filter at one end thereof is inserted into a second but larger diameter tube containing a sample of the material desired to be filtered. In U.S. Pat. No. 3,508,653, issued Apr. 28, 1970, a piston in the form of a solid plug is driven through a centrifuged blood sample so as to position itself between the serum and clot portions of the centrifuged sample. The tube within the tube concept of U.S. Pat. No. 3,512,940 suffers from the apparent deficiency of being costly and not readily adaptable for disposal after a single use. The plug arrangement of U.S. Pat. No. 3,508,653 has the shortcoming of utilizing a solid plug member which when subjected to a substantial centrifugal force, may also develop radial forces acting against the side of the sample tube, thus creating the danger of breakage.

SUMMARY OF THE INVENTION

The present invention provides a composition of matter by which the serum and clot portions of the blood sample are separated quickly and effectively by use of a simple device containing a liquid sealant consisting essentially of a silicone fluid and silica. The sealant has a specific gravity of at least 1.026 and preferably in the range of 1.030 to 1.050. As such, it will normally be at the proper specific gravity to divide the serum and clot portions of the centrifuged sample, sealing the clot in the container while the serum is removed.

Accordingly, it is an object of the present invention to provide a composition of matter for use in a simple and effective method of obtaining a serum sample during centrifuging.

DESCRIPTION OF THE DRAWINGS

FIG. 1 is an exploded partially sectional view of a sample tube and a dispenser for the composition of matter of the present invention.

FIG. 2 is a partially sectional side view of the sample tube and dispenser of FIG. 1 with the dispenser inserted into a supply of blood;

FIG. 3 is a partially sectional view similar to that of FIG. 2 wherein the blood, sample tube and dispenser have been partially subjected to centrifuging;

FIG. 4 is a view similar to FIG. 2 wherein the blood, the sample tube and dispenser have been subjected to the complete centrifuging step;

FIG. 5 is a sectional view of the sample tube with the separator in place overlying the clot portion with the serum portion removed;

FIG. 6 is an enlarged sectional view of the sealant dispenser showing the sealant contained therein;

FIG. 7 is a top view of the dispenser of FIG. 6; and

FIG. 8 is a bottom view of the dispenser of FIG. 6.

DESCRIPTION OF THE ILLUSTRATED EMBODIMENT:

Referring to the drawings, a container 10 for holding a blood sample is illustrated as a straight side wall sample tube 10 with an open top end 11. Into the open top 11 is inserted a dispenser 12. The dispenser 12 has a flange member 14 which overlies the top edge 16 of the side wall 18 of the container. The dispenser 12 includes a body portion 19 consisting of three ring sections 20, 22 and 24. Extending from the body 19 is an elongated nozzle portion 26 and at the end of the nozzle 26 is a tip 28 having an opening 30 therein. The purpose of the three rings 20, 22 and 24 is to permit the dispenser 12 to be used with containers of various diameters. Ring 20 has a shoulder 32 and a side wall 33, ring 22 a shoulder 34 and a side wall 35, and ring 24 has a shoulder 36 and a side wall 37. When using a narrow container, the dispenser bears on the top edge of the side wall of the container at one of the shoulders 32, 34 or 36 and the side wall of the next smaller ring is parallel with the inner side wall of the container. During centrifuging the relationship between the inner surface of the container and the side wall of the ring insures stability of the dispenser during this period.

By utilizing a dispenser as illustrated herein, it is possible to use one dispenser for varying diameter containers.

The body portion 19 of the dispenser has an open end 37 over which is placed a seal 38. The seal 38 has a small opening 40 therein. The seal 38 is not placed over the open end until a sealant 42 has been placed in the dispenser.

The sealant 42 consists essentially of a silicone fluid with an inert filler, such as silica, dispersed therein. The sealant should have a specific gravity of at least 1.026 and preferably in the range of 1.030 to 1.050.

The normal specific gravity of blood as determined by the pycnometric method is considered to be in the range of 1.048 to 1.066 with averages of 1.052 to 1.063. After centrifuging the specific gravity of the blood serum which separates from the remainder of the blood is at least 1.026 and in the range of 1.026 to 1.031. The specific gravity of the heavier portions such as the erythrocytes is 1.092 to 1.095.

In selecting a sealant it is necessary to select one which has a specific gravity greater than that of the serum portion. Accordingly, the sealant should have a specific gravity of at least 1.026. However, its specific gravity should not be too high so as to cause it to layer somewhere in the clot portion. Such layering would be of no practical use towards obtaining a separated serum portion. A preferred sealant would have a specific gravity in the range of 1.030 to 1.050.

The sealant is also preferably thioxtropic, water insoluble, substantially non-toxic as well as substantially chemically inert with respect to the constituents of the blood sample, particularly those in the serum portion.

A preferred sealant formulation is as follows:

Example I

| | Parts by weight |
|---|---|
| Silicone fluid (dimethylpolysiloxane) | 100 |
| Silica (specific gravity 2.65) | 8 |
| Silica (specific gravity 2.3) | 6 |

The silicone fluid used in Example I was a dimethylpolysiloxane polymer made by Union Carbide Corporation and identified by the designation "L-45". It had a viscosity of 12,500 centistokes and a specific gravity of about 0.973 at 25° C. The silica with a specific gravity of 2.65 was an amorphous silica having a particle size of at least 75% being less than 5.0 microns. It was made by Whittaker, Clark & Daniels and identified by the designation "No. 31 Lo Micron". The silica with a specific gravity of 2.3 was a hydrophobic amorphous silica having an average particle size of about 20 millimicrons. It was made by Degussa Inc. and identified by the designation "Aerosil R 972".

The silicone fluid and the silica were mixed together to a thixotropic condition with a resultant specific gravity of 1.045 to 1.050 to form the sealant.

The sealant was then placed in a dispenser of the type illustrated in FIG. 6 in particular. The diameter of the flange was 0.70 inches and the overall length 1.75 inches with the nozzle and tip being 1.10 inches. The opening in the tip was 0.032 inches. The filled dispenser was placed in a standard sample tube having an overall length of 3.875 inches with the shoulder 32 of the first ring resting on the top of the tube side wall. The tube had previously been filled with a whole blood specimen to within 1.10 inches of the open end of the tube. The extent of the dispenser from shoulder 32 to the end of the tip was 1.5 inches. Thus, the dispenser tip and part of the nozzle extended well into the blood sample.

The tube with the blood sample and dispenser was centrifuged for approximately 10 minutes. After 5 minutes substantially all of the sealant had passed from the dispenser. The sealant did not disperse but instead remained homogeneous and settled as a layer between the serum and clot portions of the centrifuged blood. It was noted that the sealant settled as a substantially even layer between the two portions since its specific gravity of 1.045 to 1.050 was less than that of the clot portion and greater than that of the serum portion. The sealant formed a tight seal against the inner wall of the tube. Also noted was the fact that the sealant had mixed into it, particularly in the portion near the clot portion, fibrant matter which had been filtered out of the serum portion as the sealant settled to its own specific gravity level.

The use of the dispenser which extended into the blood sample expedited the procedure since it was not necessary for the sealant to overcome the surface tension of the blood sample.

With the sealant in place it was possible to merely decant off the serum portion with the clot being trapped behind the sealant.

The specific gravity of the sealant was determined by using a copper sulfate method. The procedure consists of letting drops of the sealant fall into a graded series of solutions of copper sulfate of known specific gravity and noting whether the drops rise or fall. The series used were graded at 0.005 intervals. Merely by observing the drops it was possible to determine that the sealant had a specific gravity between 1.045 and 1.050.

Another sealant formulation is as follows:

Example II

| | Parts by weight |
|---|---|
| Silicone fluid (dimethylpolysiloxane) | 100 |
| Silica (specific gravity 1.95) | 14 |

The silicone fluid of Example II is the same dimethylpolysiloxane polymer of Example I. The silica with a specific gravity of 1.95 has an average particle size of 16 millimicrons. It is made by Henlig & Co. and identified by the designation "TRI-SIL 404". The specific gravity of the sealant is from 1.045 to 1.050.

Still another sealant formulation is as follows:

Example III

| | Parts by weight |
|---|---|
| Silicone fluid (ethyltriethoxysilane) | 100 |
| Silica (specific gravity 2.65) | 8 |
| Silica (specific gravity 2.3) | 20 |

The silicone fluid of Example III is an ethyltriethoxysilane monomer made by Union Carbide Corporation and identified by the designation A-15. The silicas are the same as those used in Example I.

The filler serves the dual purpose of making the silicone fluid thixotropic and of adjusting the specific gravity to that which is desired for the resultant sealant. In place of silica other inert fillers which may be used in a fine powdered form are bentonite, alumina and talc. Others will also occur to those skilled in the art.

Another silicone fluid which may be used is made by Dow Corning Corporation and identified as "200 Fluid".

In selecting silicone fluids and fillers, one should select materials which when mixed together will give the desired specific gravity, be substantially nontoxic, water insoluble and substantially chemically inert with respect to the constituents of at least the serum portion.

The dispenser serves to meter out the sealant gradually and this gradual metering provides sufficient lead time for the centrifugation to take effect before the sealant is in place. If the sealant were allowed to be positioned too soon some unwanted matter, such as red cells or fibrilar like material, may be trapped in the serum portion by the sealant.

While various examples have been described herein and one embodiment illustrated on the drawings, those skilled in the art may practice the invention in its various forms by other examples and embodiments without departing from the scope of the claims herein.

What is claimed:

1. A sealant adapted to be used in a method of separating a sample of whole blood into serum and clot portions by centrifuging wherein said sealant forms a separator between said portions, whereby the serum may be removed without disturbing the clot, said sealant consisting essentially of:
    a. a major amount of a silicone liquid; and
    b. a minor amount of an inert filler dispersed within said silicone liquid, said inert filler being used in an amount sufficient to set the specific gravity of said sealant in the range of 1.026 to 1.092, said sealant being thixotropic, water insoluble, substantially non-toxic and substantially chemically inert with respect to the constituents of the blood sample.

2. A sealant as defined in claim 1 wherein the inert filler is silica.

3. A sealant as defined in claim 2 wherein the sealant has a specific gravity in the range of 1.030 to 1.050.

4. A sealant as defined in claim 1, wherein the said inert filler is selected from the group consisting of silica, bentonite, aluminum and talc, in finely powdered form.

* * * * *